(12) United States Patent
Hausmanns et al.

(10) Patent No.: US 7,919,107 B2
(45) Date of Patent: Apr. 5, 2011

(54) METHOD FOR TREATING HYPERSENSITIVE TEETH

(75) Inventors: Stephan Hausmanns, Wiesbaden (DE); Jörg Kowalczyk, Eisenberg-Steinborn (DE); Gunhild Kozianowski, Grünstadt (DE)

(73) Assignee: Sudzucker Aktiengesellschaft Mannhein/Ochsenfurt (DE)

( * ) Notice: Subject to any disclaimer, the term of this patent is extended or adjusted under 35 U.S.C. 154(b) by 0 days.

(21) Appl. No.: 12/180,837

(22) Filed: Jul. 28, 2008

(65) Prior Publication Data

US 2010/0021508 A1    Jan. 28, 2010

(51) Int. Cl.
*A61K 8/02* (2006.01)
*A01N 59/16* (2006.01)

(52) U.S. Cl. .................................. 424/401; 424/617

(58) Field of Classification Search .............. 424/401
See application file for complete search history.

(56) References Cited

U.S. PATENT DOCUMENTS

| | | |
|---|---|---|
| 3,122,483 A | 2/1964 | Rosenthal |
| 3,689,636 A | 9/1972 | Svajda |
| 3,772,431 A | 11/1973 | Mlkvy et al. |
| 3,863,006 A | 1/1975 | Hodosh |
| 3,888,976 A | 6/1975 | Mlkvy et al. |
| 3,956,480 A | 5/1976 | Dichter et al. |
| 4,011,309 A | 3/1977 | Lutz |
| 4,057,021 A | 11/1977 | Schoppe |
| 4,631,185 A | 12/1986 | Kim |
| 4,634,589 A | 1/1987 | Scheller |
| 4,685,883 A | 8/1987 | Jernberg |
| 4,710,372 A | 12/1987 | Scheller |
| 4,751,072 A | 6/1988 | Kim |
| 4,990,327 A | 2/1991 | Neirinckx |
| 4,992,258 A | 2/1991 | Mason |
| 5,244,651 A | 9/1993 | Kayane et al. |
| 5,718,885 A | 2/1998 | Gingold et al. |
| 6,010,684 A | 1/2000 | Wiedemann |
| 6,458,400 B1 * | 10/2002 | Willibald-Ettle et al. .... 426/548 |
| 6,509,007 B2 * | 1/2003 | Rajaiah et al. ............. 424/53 |
| 2004/0086467 A1 * | 5/2004 | Curro ........................ 424/52 |
| 2005/0025720 A1 | 2/2005 | Bailey |
| 2006/0280694 A1 | 12/2006 | Peldyak et al. |
| 2006/0286044 A1 | 12/2006 | Robinson et al. |

FOREIGN PATENT DOCUMENTS

WO   WO 97/04741    2/1997
WO   WO 2004/028262   4/2004

OTHER PUBLICATIONS

International Preliminary Report on Patentability mailed Oct. 19, 2010 in corresponding International Application No. PCT/EP2009/005169.

* cited by examiner

*Primary Examiner* — Sreeni Padmanabhan
*Assistant Examiner* — Timothy E Betton
(74) *Attorney, Agent, or Firm* — Ostrolenk Faber LLP

(57) ABSTRACT

A method for imparting a teeth-desensitising effect to a food, cosmetic or pharmaceutical which comprises combining said food, cosmetic or pharmaceutical with a teeth-desensitising effective amount of a polyol.

2 Claims, 1 Drawing Sheet

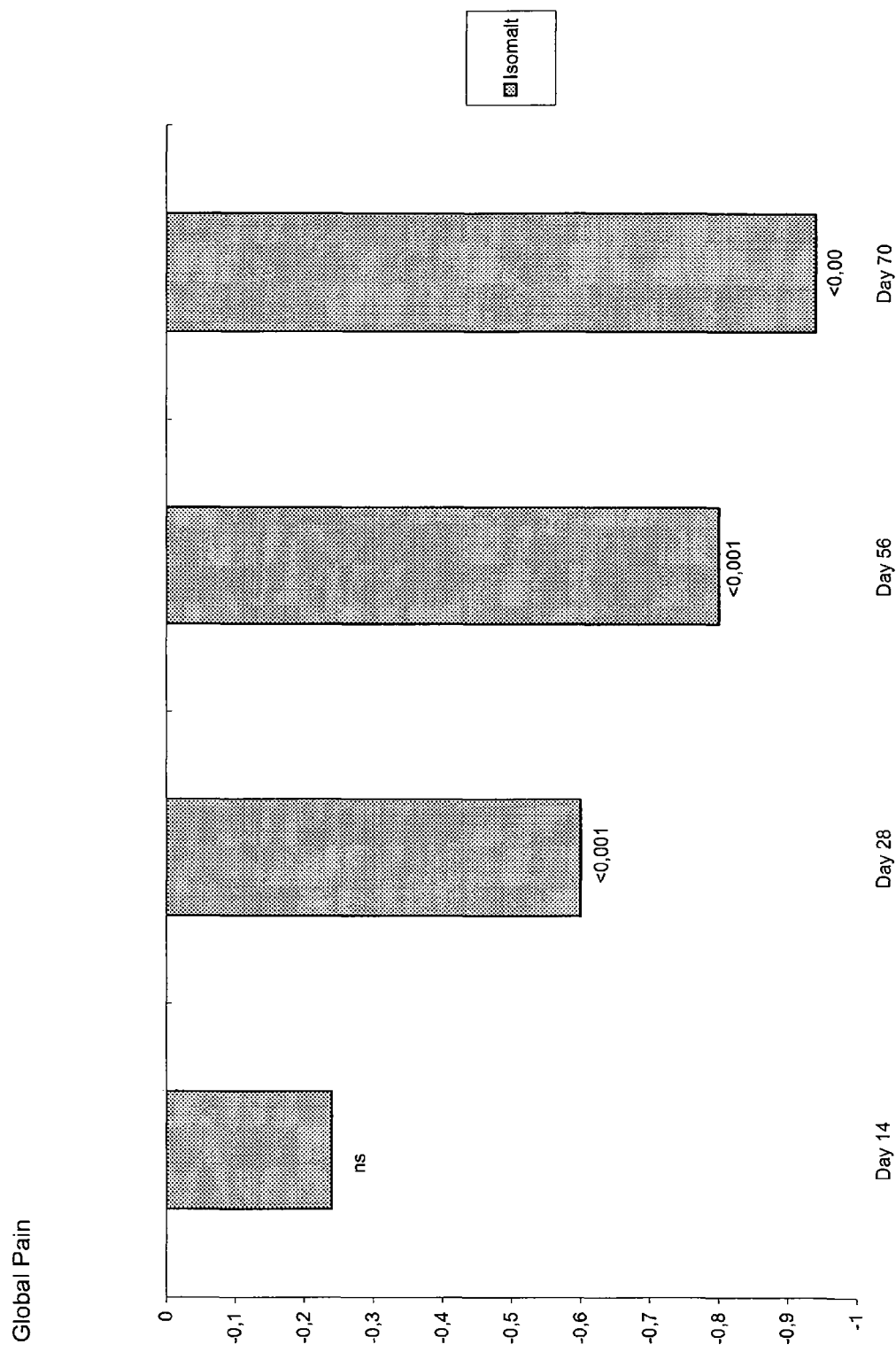

METHOD FOR TREATING HYPERSENSITIVE TEETH

TECHNICAL FIELD

The present invention relates to methods, compositions and uses to treat hypersensitive teeth of a human or animal being in need thereof.

BACKGROUND OF THE INVENTION

It is well known that the dentine layer in a tooth usually contains dentine channels. It is assumed that exposure of said channels to external stimuli may occur due to the loss of enamel and/or gingival recession. It is speculated that such exposed channels may be responsible for the phenomenon of hypersensitivity to said external stimuli such as hot or cold fluid or applied mechanical pressure.

It is well known that hypersensitive teeth may be treated by applying various agents to the surface of said teeth. U.S. Pat. No. 3,863,006 describes desensitising teeth with a nitrate salt. U.S. Pat. No. 3,689,636 describes desensitising teeth with solutions of chloride salts. U.S. Pat. No. 4,057,021 describes desensitising hypersensitive teeth by applying an aqueous solution of alkali metal salts and ammonium oxalate to the surface of the teeth. U.S. Pat. Nos. 4,631,185 and 4,751,072 describe desensitising teeth by treatment with potassium salts. U.S. Pat. Nos. 4,990,327 and 3,122,483 describe desensitising teeth with strontium ion and/or fluoride ion. U.S. Pat. No. 4,992,258 describes desensitising teeth by applying a dentifrice including a montmorillonite clay. U.S. Pat. No. 4,011,309 describes a desensitising dentifrice composition that includes citric acid, sodium citrate and non-ionic polyol surfactant. U.S. Pat. Nos. 3,888,976 and 3,772,431 describe using a zinc or strontium ion containing astringent-desensitising agent in an effervescent mouthwash tablet. U.S. Pat. No. 3,863,006 describes desensitising teeth with a nitrate salt. U.S. Pat. No. 3,689,636 describes desensitising teeth with solutions of chloride salts. U.S. Pat. Nos. 4,634,589 and 4,710,372 describe a dentifrice containing apatite particles for treating hypersensitive teeth. U.S. Pat. No. 4,685,883 describes the use of biodegradable microspheres to deliver chemotherapeutic agents to lesions and U.S. Pat. No. 3,956,480 describes treating teeth with anionic polymers complexed with a cationic germicide, such as chlorhexidine. WO 2004/028262 discloses coated chewing gums comprising poorly water soluble calcium salts or composites thereof which are able to support remineralisation of damages in the teeth.

Thus, the prior art teaches pharmaceuticals, such as tablets or solutions, which contain specifically prepared or expensive drugs for desensitising teeth. On the other hand confectionery products, such as chewing gums, are known which help to remineralise damages in teeth but which still require specific agents to achieve said aim, namely calcium salts or composites thereof. In some instances the prior art treatments rely on compounds which, for some other reasons, e.g. nutritional considerations, are already present in food, cosmetics or pharmaceuticals but whose concentration in the food has to be considerably increased in order to achieve the desired desensitising effect Thus, there still remains a need to provide further and particularly improved uses, methods and compositions which are capable of prophylactically or therapeutically desensitising teeth in an animal or human being in need thereof. This is particularly due to the consideration, that the prior art treatments to desensitise teeth involve the use of either expensive or specifically prepared or large amounts of active agents, such as minerals, salt, polymers or microspheres. Thus, it is a particular problem of the present invention to provide a teaching to desensitise teeth which uses a consumer-friendly and widely accepted food ingredient in order to specifically desensitise teeth.

SUMMARY

The technical problem underlying the present invention has been solved by the teaching of the appended claims. In particular the present invention solves its underlying technical problem by providing the teaching that a polyol, in particular a sugar alcohol, in particular isomalt, maltitol or xylitol each alone or in combination, preferably isomalt, all which are widely accepted and well-known sugar replacement agents, has the surprising and very advantageous capability of desensitising a tooth of a human or animal, in particular without the need of any further substances combined with it and without the need of using concentrations or amounts of the polyol, in particular isomalt, maltitol or xylitol, preferably isomalt, which are above the ranges conventionally employed in food, cosmetics or pharmaceuticals.

DETAILED DESCRIPTION OF CERTAIN EMBODIMENTS OF THE INVENTION

In a particularly preferred embodiment the present invention uses the capability of a polyol, in particular one or more selected from the group consisting of isomalt, maltitol and xylitol, to modify the saliva production and salivation in the mouth of the consumer in particular to increase the salivation and/or saliva production, in particular it leads to a prolonged salivation and/or saliva production.

In a particularly preferred embodiment the present invention solves its underlying problem by providing a method for imparting a tooth-desensitising effect to a food, cosmetic or pharmaceutical which comprises combining said food, cosmetic or pharmaceutical with a teeth-desensitising effective amount of a polyol, in particular one or more selected from the group consisting of isomalt, maltitol or xylitol.

In a further aspect the present invention solves its underlying problem by providing a method for prophylactically or therapeutically treating hypersensitive teeth in an animal or human being in need thereof comprising applying an effective amount of a polyol, in particular one or more selected from the group consisting of isomalt, maltitol and xylitol, to said animal or human being.

In a further aspect the present invention relates to a method for desensitising a hypersensitive tooth, comprising applying an effective amount of a polyol, in particular one or more selected from the group consisting of isomalt, maltitol and xylitol, to the surface of said tooth to cause desensitisation of said tooth.

In a further aspect the present invention solves its underlying problem by providing the use of a polyol, in particular one or more selected from the group consisting of isomalt, maltitol and xylitol, or of a preparation containing the polyol, in particular one or more selected from the group consisting of isomalt, maltitol and xylitol, for preparing a food, cosmetic or pharmaceutical for the prophylactic or therapeutic treatment of hypersensitive teeth in an animal or human being, wherein the polyol, in particular one or more selected from the group consisting of isomalt, maltitol and xylitol, is used in the pharmaceutical, cosmetic or food in an effective amount to desensitise the teeth of the animal or human being.

The present invention also relates to the use of a polyol, in particular one or more selected from the group consisting of isomalt, maltitol and xylitol, or of a preparation containing the polyol, in particular one or more selected from the group consisting of isomalt, maltitol and xylitol, for prophylactically or therapeutically treating hypersensitive teeth, in particular for desensitising hypersensitive teeth.

The present invention also relates to a food, cosmetic or pharmaceutical for treating hypersensitive teeth comprising a polyol, in particular one or more selected from the group consisting of isomalt, maltitol and xylitol, wherein the polyol, in particular one or more selected from the group consisting of isomalt, maltitol and xylitol, is determined for and capable of treating the hypersensitive teeth. The invention also relates to a polyol, in particular one or more selected from the group consisting of isomalt, maltitol and xylitol, for treating hypersensitive teeth. The invention also relates to a polyol, in particular one or more selected from the group consisting of isomalt, maltitol and xylitol, for use as a teeth desensitising agent, in particular in a food, cosmetic or pharmaceutical.

In the context of the present invention the term "one or more selected from the group consisting of" is meant to explicitly identify any individual member of said group and a combination of at least two of said members. A "combination" from the group of isomalt, maltitol and xylitol, in particular of at least two of isomalt, maltitol or xylitol is meant to mean a) isomalt and maltitol, b) isomalt and xylitol, c) maltitol and xylitol or d) isomalt, maltitol and xylitol.

In a particularly preferred embodiment the present invention uses the capability of isomalt to modify the saliva production and salivation in the mouth of the consumer in particular increases the salivation and/or saliva production, in particular leads to a prolonged salivation and/or saliva production.

In a particularly preferred embodiment the present invention solves its underlying problem by providing a method for imparting a toothdesensitising effect to a food, cosmetic or pharmaceutical which comprises combining said food, cosmetic or pharmaceutical with a teeth-desensitising effective amount of isomalt.

In a further aspect the present invention solves its underlying problem by providing a method for prophylactically or therapeutically treating hypersensitive teeth in an animal or human being in need thereof comprising applying an effective amount of isomalt to said animal or human being.

In a further aspect the present invention relates to a method for desensitising a hypersensitive tooth, comprising applying an effective amount of isomalt to the surface of said tooth to cause desensitisation of said tooth.

In a further aspect the present invention solves its underlying problem by providing the use of isomalt or of an isomalt-containing preparation for preparing a food, cosmetic or pharmaceutical for the prophylactic or therapeutic treatment of hypersensitive teeth in an animal or human being, wherein the isomalt is used in the pharmaceutical, cosmetic or food in an effective amount to desensitise the teeth of the animal or human being.

The present invention also relates to the use of isomalt or of an isomalt-containing preparation for prophylactically or therapeutically treating hypersensitive teeth, in particular for desensitising hypersensitive teeth.

The present invention also relates to a food, cosmetic or pharmaceutical for treating hypersensitive teeth comprising isomalt, wherein the isomalt is determined for and capable of treating the hypersensitive teeth. The invention also relates to isomalt for treating hypersensitive teeth. The invention also relates to isomalt for use as a teeth desensitising agent, in particular in a food, cosmetic or pharmaceutical.

Thus, the present invention provides the advantageous teaching that a polyol, in particular isomalt, maltitol or xylitol, alone or in a combination, preferably isomalt alone, in addition to its conventional use as an akariogenic sugar replacement agent can be used specifically for the purpose to treat hypersensitive teeth, i.e. to desensitise teeth in a human or animal being. Thus, the present invention provides the skilled person with the technical teaching to treat in a prophylactic or therapeutic way hypersensitive teeth by applying to the consumer's teeth, in particular the surface of a tooth, an effective amount of a polyol, in particular isomalt, maltitol or xylitol, alone or in a combination, preferably isomalt alone, so as to desensitise the tooth. In a particularly preferred embodiment the amounts of the polyol, in particular isomalt, maltitol or xylitol, alone or in a combination, preferably isomalt alone, to be applied are those amounts which are conventionally used when the polyol, in particular isomalt, maltitol or xylitol, alone or in a combination, preferably isomalt alone, is employed as a conventional sugar replacement agent in various food, cosmetics or pharmaceuticals. The present teaching opens up to the skilled artisian an advantageous possibility to treat hypersensitive teeth and thereby avoids the necessity to use cost-intensive, potentially toxic (e.g. strontium salts) or specifically prepared ingredients which would—without the need for treating hypersensitive teeth— not be present in the food, cosmetic or pharmaceuticals or at least not in the amounts employed.

In the context of the present invention isomalt is understood to mean any mixture of 1.1-GPM (1-O-$\alpha$-D-glucopyranosyl-D-mannitol) and 1.6-GPS (6-O-$\alpha$-D-glucopyranosyl-D-sorbitol), in particular any mixture comprising 1 to 99 weight % 1.1-GPM to 99 to 1% 1.6-GPS (all values given in weight-% on dry matter). In a particularly preferred embodiment isomalt can be standard isomalt (isomalt ST) which is an equimolar or nearly equimolar mixture of 1.1-GPM and 1.6-GPS. In a preferred embodiment, isomalt is a mixture of 43 to 57% 1,6-GPS and 57 to 43% 1,1-GPM, preferably an equimolar 1.1 mixture (values given in weight-% on dry matter).

In a further preferred embodiment the term isomalt as used in the present invention is meant to also comprise isomalt variants. Such isomalt variants may in a preferred embodiment be isomalt GS, a 1.6-GPS-enriched mixture, a 1.1-GPM-enriched mixture or 1.1-GPM and 1.6-GPS containing mixtures which in addition comprise 1.1-G PS (1-O-$\alpha$-D-glucopyranosyl-D-sorbitol).

In the context of the present invention isomalt GS is a mixture of 1,6-GPS and 1,1-GPM in a ratio from 71 to 79% 1,6-GPS and 21 to 29% 1,1-GPM, preferably 75% 1,6-GPS to 25% 1,1-GPM.

In a particularly preferred embodiment a 1.1-GPM-enriched mixture is a mixture comprising 1.1-GPM and 1.6-GPS, wherein the mixture comprises more than 57 to 99 weight % 1.1-GPM and less than 43 to 1 weight % 1.6-GPS. In the context of the present invention a 1.6-GPS-enriched mixture is a mixture comprising 1.1-GPM and 1.6-GPS, wherein the amount of 1.1-GPM is less than 43 weight % to 1% and the amount of 1.6-GPS is from more than 57 to 99 weight % (all values given in weight-% on dry matter).

In a furthermore preferred embodiment of the present invention, the isomalt used is a milled and agglomerated isomalt, in particular a milled and agglomerated isomalt, wherein the milled isomalt particles have a diameter less that 100 µm, preferably less than 50 µm. Preferably, such a milled and agglomerated isomalt is isomalt DC.

In a preferred embodiment of the present invention, the isomalt, in particular standard isomalt or isomalt GS, is used in form of particles, wherein 90% of said particles have a diameter of less than 100 µm, preferably less than 50 µm.

Particle size as described herein is measured by scanning electron microscopy (SEM) or other optical or screening techniques, for example using a coulter counter.

In a preferred embodiment of the present invention a food is understood to be any material, in particular often containing carbohydrates, protein, water and/or fat, which is suitable to be consumed primarily for nutritional purposes, possibly also for pleasure, by a human or animal being. In particular a food according to the present invention may be solid, semi solid or liquid. In particular a food according to the present invention can in a preferred embodiment be also a confectionery product, sometimes also called a sweet or luxury food. In a further preferred embodiment the food may also be a baked good, a functional food, a cereal, a dairy product, a fruit-based product, an enteral nutrition, an extract, a concentrate, a beverage, or a coated product.

In a particularly preferred embodiment the pharmaceutical mentioned in the present invention may be any composition which is determined and suitable for prophylactically or therapeutically treating a human or animal being in need of such a treatment. Such a pharmaceutical may comprise a pharmaceutically acceptable carrier, optionally at least one auxiliary substance and in accordance with the present invention a polyol, in particular isomalt, maltitol or xylitol, each alone or in combination, preferably isomalt. In a particularly preferred embodiment such a pharmaceutical may in a preferred embodiment be in the form of a tablet, dentifrice, a paste, a liquid, a capsule, a gel or a coated tablet or coated capsule.

In a particularly preferred embodiment the cosmetics mentioned in the present invention are substances or compositions used to enhance or protect the appearance or odour of the human or animal body. Cosmetics comprise powders, teeth whiteners, mouth water, lotions, crèmes, skin care preparations, lip sticks, facial make-up, baby products, face oils, butters or gels.

In the context of the present invention, the term "composition" is meant to relate to a food, cosmetic and a pharmaceutical.

In case the polyol containing compositions, in particular the isomalt, maltitol or xylitol containing composition is a coated product the pre-sent invention foresees in a particularly preferred embodiment such a coated product, use thereof or a method employing it, which employs the polyol, in particular isomalt, maltitol or xylitol, preferably isomalt, as a tooth desensitising agent, wherein the polyol, in particular isomalt, maltitol or xylitol, preferably isomalt, is the only teeth desensitising agent present in the coating of the product. In a particularly preferred embodiment the coated product does not employ any other agent in the coating which is suitable to provide a teeth desensitising effect. In a particularly preferred embodiment the present invention therefore foresees a coated product, method employing it or use thereof wherein the coating comprises the polyol, in particular isomalt, xylitol or maltitol, preferably isomalt, but is free of calcium, in particular calcium salts or calcium compositions. In a furthermore preferred embodiment the present invention relates to a coated product, a method employing it or a use thereof, wherein the coating of the coated product comprises the polyol, in particular isomalt, xylitol or maltitol, preferably isomalt, but is free of calcium phosphate salts. In a furthermore preferred embodiment the present invention foresees a coated product, a method employing it or a use thereof, wherein the coating of the coated product coating comprises the polyol, in particular isomalt, xylitol or maltitol, preferably isomalt, but is free of arginine-containing complexes. In a furthermore preferred embodiment the present invention relates to a coated product, a method employing it or a use thereof, wherein the coating of the coated product comprises the polyol, in particular isomalt, xylitol or maltitol, preferably isomalt, but is free of nerve desensitising agents, such as a potassium salt, strontium salts or combination of zinc or strontium ions or mixtures thereof. In a furthermore preferred embodiment the present invention relates to a coated product, a method employing it or a use thereof, wherein the coating of the coated product comprises the polyol, in particular isomalt, xylitol or maltitol, preferably isomalt, but is free of enzymes or modified enzymes. In a furthermore preferred embodiment the present invention relates to a coated product, a method employing it or a use thereof, wherein the coating of the coated product comprises the polyol, in particular isomalt, xylitol or maltitol, preferably isomalt, but is free of bioactive glass particles, in particular free of any glass particles. In a furthermore preferred embodiment the present invention relates to a coated product, a method employing it or a use thereof, wherein the coating of the coated product comprises the polyol, in particular isomalt, xylitol or maltitol, preferably isomalt, but is a) free of sucrose, b) free of glucose, c) free of lactose, d) free of maltose, e) free of fructose or f) free of all or a sub combination of said sugars.

In a particularly preferred embodiment the present invention foresees a composition, a use or a method employing a polyol, in particular isomalt, maltitol or xylitol, preferably isomalt, as a teeth desensitising agent, wherein the polyol, in particular isomalt, maltitol or xylitol, preferably isomalt, is the only teeth desensitising agent employed in the method, use or composition. In a particularly preferred embodiment the use, method or composition does not employ any other agent which is suitable to provide a teeth desensitising effect. In a particularly preferred embodiment the present invention therefore foresees a method, a use or a composition which is free of calcium, in particular calcium salts or calcium compositions. In a furthermore preferred embodiment the present invention relates to methods, uses and compositions which are free of calcium phosphate salts. In a furthermore preferred embodiment the present invention foresees methods, uses or compositions which are free of arginine-containing complexes. In a furthermore preferred embodiment the method, use or composition of the present invention is free of nerve desensitising agents, such as a potassium salt, strontium salts or combination of zinc or strontium ions or mixtures thereof. In a furthermore preferred embodiment the present invention relates to methods, uses and compositions which are free of enzymes or modified enzymes. In a furthermore preferred embodiment the present invention relates to methods, uses and compositions which are free of bioactive glass particles, in particular free of any glass particles. In a furthermore preferred embodiment the present invention relates to methods, uses or compositions which are a) free of sucrose, b) free of glucose, c) free of lactose, d) free of maltose, e) free of fructose or f) free of all or a sub combination of said sugars.

In a particularly preferred embodiment of the present invention the method, use or composition, in particular the confectionery product, is employing as the only sugar alcohol isomalt, i.e. is free of any other sugar alcohol.

In a particularly preferred embodiment of the present invention the coated composition of the present invention or a method of employing or using it, in particular the coated confectionery product, is employing as the only sugar alcohol in its coating isomalt, i.e. the coating is free of any other sugar alcohol.

In a preferred embodiment of the present invention, the method, use or composition, in particular the confectionery product, is sugar-free.

In a preferred embodiment of the present invention, the coating of the coated composition of the present invention or a method of employing or using it, in particular the coating of the coated confectionery product, is sugar free.

In a preferred embodiment of the present invention, the method, use or composition, in particular the confectionery product, is tooth-friendly.

In a furthermore preferred embodiment, it is evident that depending upon the specific nature of the food, in particular the confectionery product, cosmetic or pharmaceutical product additives may be present in the food, cosmetic or pharmaceutical or its coating.

In the context of the present invention, a product additive is any sub-stance which may be added into the preparation process to either influence the preparation process itself and/or influence product characteristics, which may either be relevant for the process or for the finally obtained product, for instance its organoleptic, sensoric, physiological, storage or optical behaviour or its nutritional value.

In a particularly preferred embodiment the food, cosmetic or pharmaceutical of the present invention comprises 5 to 100 weight %, in particular 10 to 80 weight %, preferably 20 to 70 weight %, in particular 40 to 99.9 weight %, preferably 45 to 90 weight %, preferably 60 to 99 weight % and preferably 30 to 60 weight % of the polyol, in particular isomalt, xylitol or maltitol, each alone or in combination, preferably isomalt (each time weight % based on dry matter of entire product), the remainder to 100 weight % adding up with product additives.

In a particularly preferred embodiment in case the food, cosmetic or pharmaceutical is a coated product it is in a preferred embodiment foreseen that the coating comprises 70 to 100 weight %, preferably 80 to 99 weight %, preferably 50 to 95 weight %, in particular 50 to 75 weight-%, preferably 80 to 99 weight-%, preferably 85 to 99 weight %, most preferably 90 to 99 weight-% of the polyol, in particular isomalt, xylitol or maltitol, each alone or in combination, preferably isomalt (each time weight % based on dry matter of coating), the remainder to 100 weight % adding up with product additives, in particular high intensity sweeteners, gum arabic or gelatine and colours.

Depending upon the nature of the food or, in particular confectionery product, cosmetic or pharmaceutical it comprises in addition to the polyol, in particular isomalt, xylitol or maltitol, each alone or in combination, preferably isomalt, 0 to 95 weight %, in particular 0 to 75 weight-%, preferably 30 to 80 weight %, preferably 40 to 70 weight % and preferably 0.1 to 60 weight-%, preferably 10 to 55 weight-% (all % given in weight % on dry matter of entire product), most preferably 1 to 40 weight-% of product additives, all of them adding up to 100% with the polyol, in particular isomalt, xylitol or maltitol, each alone or in combination, preferably isomalt content.

In a preferred embodiment of the present invention, the product additive is selected from the group consisting of intense sweeteners, hydrocolloid, gum base, plastifiers, lubricant, emulsifiers, protein, protein components, milk components, plant materials, carbohydrates, flour, bulking agents, dairy ingredients, fruits, vegetables, fat and fat substitutes, vegetable fat, vitamins, minerals, pharmaceutically active ingredients, preservatives, aroma, flavourings, such as peppermint, menthol, fruit, strawberry flavour, colours, $TiO_2$, water, edible acids, such as citric acid, and dietary fibres.

In a preferred embodiment of the present invention, the intense sweetener is selected from the group of cyclamate, saccharin, aspartame, glycyrrhicine, neohesperidine-dihydrochalcone, steveoside, rebaudioside A, thaumatin, monellin, acesulfame, alitame, sucralose or a mixture thereof.

In a preferred embodiment of the present invention, the food, in particular confectionery product, is selected from the group of chewing gums, hard caramels, soft caramels, toffee, pastille, tablets, gum, jellies, marshmallows, lozenges, fudge and fondant.

In a furthermore preferred embodiment the confectionery product may be a non-coated product, in particular a chewing gum, for instance a chewing gum strip.

In the context of the present invention, a tablet is a compressed product, i.e. a product prepared by mixing its ingredients in dry and powdered from and exerting pressure on said mixture to obtain a solid so-called compressed product.

In the context of the present invention, a hard candy and a soft candy is also called a hard caramel and a soft caramel.

In a preferred embodiment of the present invention, the confectionery product is a coated product.

In a particularly preferred embodiment it is foreseen that the polyol, in particular isomalt, maltitol or xylitol, each alone or a combination thereof, in particular isomalt, is—in case the food, cosmetic or pharmaceutical of the present invention is a coated product—present in said coating, either exclusively or partially. In a particularly preferred embodiment the coating is made exclusively, i.e. solely from the polyol, in particular isomalt, maltitol or xylitol, each alone or a combination thereof, in particular isomalt. In a furthermore preferred embodiment it, of course, can also be foreseen that in addition to the polyol, in particular isomalt, maltitol or xylitol, each alone or a combination thereof, in particular isomalt, additives are present in the coating. In a preferred embodiment such additives, which in addition to the polyol, in particular isomalt, maltitol or xylitol, each alone or a combination thereof, in particular isomalt, are present in such a coating are colours and high-intensity sweeteners and optionally gum arabic or gelatine.

In a preferred embodiment of the present invention, the coated product is a coated chewing gum, a coated toffee, a coated jelly, a coated tablet or a coated soft caramel.

In a preferred embodiment of the present invention, the coated product comprises 15 to 70, preferably 25 to 45, weight-% product coating (based on dry weight of the overall coated product). Preferably, the coated product comprises 30 to 85, preferably 55 to 75 weight-% product core (based on the dry weight of the overall coated product).

In a particularly preferred embodiment, the product coating may comprise 1, 2 or more, for instance 50 to 100 layers of product coating material. In a particularly preferred embodiment, said layers may be of the same or different compositions.

Further preferred embodiments are the subject matter of the subclaims.

EXAMPLES

The invention will now be illustrated in more detail by the following examples and the drawing illustrating said example. The examples are provided only for the purpose of illustrating the invention and are not to be construed as limiting.

BRIEF DESCRIPTION OF THE FIGURE

The drawing shows the graphic presentation of a statistic evaluation of pain sensitivity tests.

EXAMPLE 1

Preparation of isomalt comprising coated chewing gum:
Recipe for coating syrup:

| Batch size: 7.5 kg chewing gum centres | |
|---|---|
| Isomalt GS | 6500 g |
| Water | 3364 g |
| Gelatine | 26 g |
| Aspartam | 5 g |
| Acesulfam K | 5 g |
| Titanium dioxide | 100 g |
| Total | 10000 g |

Drycharge:
Isomalt ST/PF: Phase 1: 1×100 g; Phase 2: 5×80 g
Flavour: H&R Optamint, in Phase 3: 2×25 g, Glazing agent: polishing wax (Fa. Kahl), Syrup Temperature: 65° C.
Syrup Preparation:
First Isomalt GS is dissolved in water then the other ingredients are added to the syrup. After preparation the syrup is kept at 65° C.
Coating Process:
Equipment: Driacoater 500/600 Vario

| Phase | Cycle | Total syrup amount [g] | Syrup amount per cycle [g] | Drycharge [g] |
|---|---|---|---|---|
| 1 | 1 | 120 | 120 | 1 × 100 |
| 2 | 5 | 450 | 90 | 5 × 80 |
| 3 | 2 | 200 | 100 | Flavour (2 × 25 g) |
| 4 | 45 | 4500 | 100 | — |
| 5 | 6 | 480 | 80 | — |
| 6 | 2 | 140 | 70 | — |
| 7 | 1 | 60 | 60 | — |
| 8 | 1 | Glazing | — | — |

Thickness of coat: 33.7%; Coating time: 187 min

EXAMPLE 2

Preparation of a non-coated chewing gum strip containing a sweetener mixture of 1.6-GPS, 1.1-GPS and 1.1-GPM.
Formula:

| | |
|---|---|
| basic chewing gum compound NOSTIC TWA | 1.50 kg |
| sweetener mixture composed of 1.6-GPS, 1.1-GPS and 1.1-GPM (37 weight % 1.6-GPS, 2 weight % 1.1-GPS, 61 weight % 1.1-GPM, based on the dry weight of the sweetener mixture) | 2.50 kg |
| sorbitol syrup (70% dry substance) | 0.60 kg |
| glycerol | 0.15 kg |
| menthol | 0.15 kg |
| flavouring (Spearmint) | 0.10 kg |
| aspartame | 2.5 g |
| acesulfame-K | 2.5 g |

Preparation:
The basic chewing gum compound is heated in a heating cabinet at temperatures of 50° C. to 55° C. prior to its transfer into the kneader. Then the basic chewing gum compound is kneaded for 1 to 2 min. During the kneading, the first half of the sweetener mixture, after that, glycerol are added and, finally, the flavouring, menthol and the sweetener. The mixture is kneaded until it has become homogeneous (final temperature approximately 45° C.). The mass is removed from the kneader and subdivided into portions of about 1 kg weight. The subdivided chewing gum mass is placed for intermediate storage for about 15 to 20 min on a substrate sprinkled with talcum, is extruded with an appropriate extruder and processed further in the conventional manner.

EXAMPLE 3

Chewing gum consumption reduces hypersensitivity of teeth. 50 probands suffering from hypersensitivity against cold took part in this study. For eight weeks until day 56 (see table below), three times a day (in the morning, at noon and in the evening) they chewed for 10 minutes an isomalt-containing chewing gum according to example 1.

Following this treatment period for further two weeks subjects were monitored (regression phase). At visits at the start day 0, day 14, day 28, day 56 (end of treatment) and day 70, global pain sensation since the last visit was asked.

Each time after brushing their teeth their feeling of global pain was noted.

The results are given in the table.

| Day of examination | Score, absolut | Score, Δ to day 0 |
|---|---|---|
| −7/−21 days prior to treatment | 5.26 | |
| day 0 | 5.12 | — |
| day 14 | 4.88 | −0.24 |
| day 28 | 4.52 | −0.60 |
| day 56 | 4.32 | −0.80 |
| day 70 | 4.18 | −0.94 |

Score: 0: no pain, 8: very strong pain
On days −7 and −21, which are one and three weeks before the beginning of the consumption of the chewing gums, the feeling of global pain was 5.26, which is considered to be the negative control value.

Already on day 14 after having started with the chewing gum consumption significant reductions in the global pain feeling showing a reduced hypersensitivity could be noted. This effect improved over the following weeks until the end of the study on day 70.

The FIGURE shows the results graphically. Thus, the consumption of isomalt-containing chewing gums clearly and substantially reduces a hypersensitivity in teeth of human beings.

What is claimed is:

1. A method for desensitizing a hypersensitive tooth, said method comprising contacting a surface of a hypersensitive tooth with a polyol effective to cause desensitization of said tooth, wherein the polyol is the only agent contacted with said hypersensitive tooth that is suitable for providing a tooth desensitizing effect to said tooth.

2. A method for desensitizing a hypersensitive tooth, said method comprising applying a food, cosmetic or pharmaceutical to a surface of said tooth, wherein the food, cosmetic or pharmaceutical is a product coated with a polyol and the polyol is effective to cause desensitization of said tooth.

* * * * *